US009579322B2

(12) United States Patent
Alam

(10) Patent No.: US 9,579,322 B2
(45) Date of Patent: Feb. 28, 2017

(54) METHODS FOR TREATING NEUROLOGIC DISORDERS

(71) Applicant: EIP Pharma, LLC, Cambridge, MA (US)

(72) Inventor: John Jahangir Alam, Cambridge, MA (US)

(73) Assignee: EIP Pharma, LLC, Cambridge, MA (US)

( * ) Notice: Subject to any disclaimer, the term of this patent is extended or adjusted under 35 U.S.C. 154(b) by 0 days.

(21) Appl. No.: 14/794,469

(22) Filed: Jul. 8, 2015

(65) Prior Publication Data

US 2016/0008364 A1    Jan. 14, 2016

Related U.S. Application Data

(60) Provisional application No. 62/022,586, filed on Jul. 9, 2014.

(51) Int. Cl.
*A61K 31/519* (2006.01)
*A61P 25/28* (2006.01)
*A61K 31/00* (2006.01)

(52) U.S. Cl.
CPC ............ *A61K 31/519* (2013.01); *A61K 31/00* (2013.01)

(58) Field of Classification Search
CPC .................................................. A61K 31/519
See application file for complete search history.

(56) References Cited

U.S. PATENT DOCUMENTS

| 7,956,198 | B2 | 6/2011 | Sattigeri et al. |
| 8,304,413 | B2 | 11/2012 | Kossen et al. |
| 8,697,627 | B2 | 4/2014 | Alam |
| 2005/0203111 | A1 | 9/2005 | David |
| 2012/0289511 | A1 | 11/2012 | Alam |
| 2014/0357638 | A1 | 12/2014 | Alam |
| 2016/0030431 | A1 | 2/2016 | Alam |

FOREIGN PATENT DOCUMENTS

| CN | 1244867 A | 2/2000 |
| JP | 2007-528393 A | 10/2007 |
| JP | 2009-541483 A | 11/2009 |
| WO | WO-98/27098 A1 | 6/1998 |
| WO | WO-2005/091891 A2 | 10/2005 |
| WO | WO-2008/002465 A2 | 1/2008 |
| WO | WO 2012/154814 | * 11/2012 |
| WO | WO-2016/007616 A1 | 1/2016 |

OTHER PUBLICATIONS

Hoshino, "Reducing amyloid plaque burden associated with Alzheimer's disease", J Neurochemistry, 120(5), 2012, pp. 795-805.*
Alonso, M. et al., Memory formation requires p38MAPK activity in the rat hippocampus, Neuroreport., 14(15):1989-92 (2003).
Bach et al., The Role of CNI-1493 in the Function of Primary Microglia with Respect to Amyloid-β, Journal of Alzheimer's Disease, 26:69-80 (2011).
Bacher et al., CNI-1493 inhibits Aβ production, plaque formation, and cognitive deterioration in an animal model of Alzheimer's disease, The Journal of Experimental Medicine, 205(7):1593-1599 (2008).
Bachstetter, A.D. et al., Attenuation of traumatic brain injury-induced cognitive impairment in mice by targeting increased cytokine levels with a small molecule experimental therapeutic, J. Neuroinflammation, 12:69, 9 pages (2015).
Bachstetter, A.D. et al., Early stage drug treatment that normalizes proinflammatory cytokine production attenuates synaptic dysfunction in a mouse model that exhibits age-dependent progression of Alzheimer's disease-related pathology, J. Neurosci., 32(30):10201-10 (2012).
Bachstetter, A.D. et al., The p38α MAPK regulates microglial responsiveness to diffuse traumatic brain injury, J. Neurosci., 33(14):6143-53 (2013).
Bain et al., The selectivity of protein kinase inhibitors: a further update, Biochem. J., 408:297-315 (2007).
Barrientos, R.M. et al., Aging-related changes in neuroimmune-endocrine function: Implications for hippocampal-dependent cognition, Horm. Behav., 62(3):219-227 (2012).
Bhaskar et al., Regulation of Tau Pathology by the Microglial Fractalkine Receptor, Neuron 68:19-31 (2010).
Brown, K.K. et al., P38 MAP kinase inhibitors as potential therapeutics for the treatment of joint degeneration and pain associated with osteoarthritis, Journal of Inflammation, 5(22):1-8 (2008).
Castello, M.A. et al., Moving beyond anti-amyloid therapy for the prevention and treatment of Alzheimer's disease, BMC Neurology, 14:169, 5 pages (2014).
Chlan-Fourney, J. et al., The increased density of p38 mitogen-activated protein kinase-immunoreactive microglia in the sensorimotor cortex of aged TgCRND8 mice is associated predominantly with smaller dense-core amyloid plaques, European Journal of Neuroscience, 33(8):1433-1444 (2011).
Chopra, P. et al., Pharmacological profile of AW-814141, a novel, potent, selective and orally active inhibitor of p38 MAP kinase, International Immunopharmacology, 10:467-473 (2010).
Clark, C.M. et al., Use of florbetapir-PET for imaging beta-amyloid pathology, JAMA, 305(3):275-83 (2011).
Correa, S.A.L. and Eales, K. L., the Role of p38 MAPK and Its Substrates in Neuronal Plasticity and Neurodegenerative Disease, Journal of Signal Transduction, Hindawi Publishing Corporation, vol. 2012, Article ID 649079, 12 pages (2012).
Duffy, J.P. et al., The Discovery of VX-745: A Novel and Selective p38-alpha Kinase Inhibitor, ACS Med. Chem. Lett., 2:758-763 (2011).
Fiore, K., Another Drug Moves Amyloid Without Clinical Effects-Study highlights amyloid-Alzheimer's 'disconnect', MedPage Today, 4 pages (2015).
Garcia-Alloza, M. et al., Existing plaques and neuritic abnormalities in APP:PSI mice are not affected by administration of the gamma-secretase inhibitor LY-411575, Molecular Neurodegeneration, 4(19):1-9 (2009).
Godl et al., An efficient proteomics method to identify the cellular targets of protein kinase inhibitors, PNAS, 100(26):15434-15439 (2003).

(Continued)

*Primary Examiner* — Sahar Javanmard
(74) *Attorney, Agent, or Firm* — Robert N. Sahr; Nishat A. Shaikh; Choate Hall & Stewart LLP

(57) ABSTRACT

The present invention provides methods for treating a neurological disorder.

7 Claims, 6 Drawing Sheets

(56) References Cited

OTHER PUBLICATIONS

Goldstein, D.M. et al., Selective p38alpha inhibitors clinically evaluated for the treatment of chronic inflammatory disorders, J. Med. Chem., 53(6):2345-53 (2010).
Haddad, VX-745 Vertex Pharmaceuticals, Current Opinion in Investigational Drugs, 2(8):1070-1076, (2001).
Herrup, K., The case for rejecting the amyloid cascade hypothesis, Perspective, Nature Neuroscience, 18(6):794-799 (2015).
Hideshima, T. et al., Targeting p38 MAPK inhibits multiple myeloma cell growth in the bone marrow milieu, Blood, 101(2):703-5 (2003).
Hull, M. et al., Pathways of Inflammatory Activation in Alzheimer's Disease: Potential Targets for Disease Modifying Drugs, Current Medicinal Chemistry, 9(1): 83-88 (2002).
Kumar, S. et al., p38 MAP kinases: key signalling molecules as therapeutic targets for inflammatory diseases, Nat. Rev. Drug Discov., 2(9):717-26 (2003).
Lachman, H.J. et al., Natural History and Outcome in Systemic AA Amyloidosis Abstract Background, New England Journal of Medicine, 2361-2371 (2007).
Lee et al., CX3CR1 Deficiency Alters Microglial Activation and Reduces Beta-Amyloid Deposition in Two Alzheimer's Disease Mouse Models, The American Journal of Pathology, 177(5):2549-2562(2010).
Li, S. et al., Soluble A-beta oligomers inhibit long-term potentiation through a mechanism involving excessive activation of extrasynaptic NR2B-containing NMDA receptors, J. Neurosci., 31(18):6627-38 (2011).
Lowenberg et al., Specific Inhibition of c-Raf Activity by Semapimod Induces Clinical Remission in Severe Crohn's Disease, The Journal of Immunology, 175:2293-2300 (2005).
Matousek, S. B. et al., Chronic IL-1?-mediated neuroinflammation mitigates amyloid pathology in a mouse model of Alzheimer's disease without inducing overt neurodegeneration, J. Neuroimmune Pharmacol., 7(1): 156-164 (2012).
Mayer et al., p38 MAP kinase inhibitors: A future therapy for inflammatory diseases, Drug Discovery Today: Therapeutic Strategies, 3(1):49-54 (2006).
McAfoose, J. and Baune, B.T., Evidence for cytokine model of cognitive function, Neuroscience and Biobehavioral Reviews, 33:355-366 (2009).
Merlini, G. and Bellotti, V., Molecular mechanisms of amyloidosis, The New England Journal of Medicine, 349(6):583-596 (2003).
Minoshima, S. et al., Metabolic reduction in the posterior cingulate cortex in very early Alzheimer's disease, Ann. Neurol., 42(1):85-94 (1997).
Munoz et al., Targeting p38 MAPK pathway for the treatment of Alzheimer's disease, Neuropharmacology, 58:561-568 (2010).
Munoz, L. and Ammit, A.J., Targeting p38 MAPK pathway for the treatment of Alzheimer's disease, Neuropharmacology, 58:561-568 (2010).
Paul, M., Promising New Alzheimer's 'Drug' Halts Memory Loss, 'Drug' strikes newly identified target and could be used early in disease, Northwestern Univeristy News, 3 pages (2013) Online, last accessed Apr. 23, 2015 <http://www.northwestern.edu/newscenter/stories/2013/06/promising-new-alzheimers-drug-halts-memory-loss.html>.

Reagan-Shaw et al., Dose translation from animal to human studies revisited, The FASEB Journal, 22:659-661 (2007).
Regan et al., Pyrazole Urea-Based Inhibitors of p38 MAP Kinase: From Lead Compound to Clinical Candidate, J. Med. Chem., 45:2994-3008 (2002).
Roh, et al., Stealth Attack: Plaque-Specific Antibody Allows for Efficient A? Removal without Side Effects, Neuron, 76:859-861 (2012).
Roy, S.M. et al., Targeting human central nervous system protein kinases: An isoform selective p38?MAPK inhibitor that attenuates disease progression in Alzheimer's disease mouse models, ACS Chem. Neurosci., 6(4):666-80 (2015).
Schnöder, L. et al., Deficiency of Neuronal p38a-MAPK Attenuates Amyloid Pathology in Alzheimer's Mouse and Cell Models through Facilitating Lysosomal Degradation of BACE1, J. Biol. Chem., 27 pages (2015).
Tse et al., Targeting pre-existing plaques in AD, Nature Reviews Drug Discovery, 12:100-101 (2013).
Verkaar, F. et al., Inhibition of Wnt/$\beta$-catenin signaling by p38 MAP kinase inhibitors is explained by cross-reactivity with casein kinase $1\delta/\epsilon$, Chem. Biol., 18(4):485-94 (2011).
Villemagne, V.L. et al., Longitudinal assessment of A? and cognition in aging and Alzheimer disease, Ann. Neurol., 69(1):181-92 (2011).
Wadsworth, S.A. et al., RWJ 67657, a Potent, Orally Active Inhibitor of p38 Mitogen-Activated Protein Kinase, The Journal of Pharmacology and Experimental Therapeutics, 291(2):680-687 (1999).
Wang, D.S. et al., Memory deficits induced by inflammation are regulated by alpha5-subunit-containing GABAA receptors, Cell Rep., 2(3):488-96 (2012).
Watterson, D.M. et al., Development of Novel in Vivo Chemical Probes to Address CNS Protein Kinase Involvement in Synaptic Dysfunction, PLoS One, 8(6):e66226 (2013).
Weisman et al., A Double-Blind, Placebo-Controlled Trial of VX-745, an Oral p38 Mitogen Activated Protein Kinase (MAPK) Inhibitor, in Patients with Rheumatoid Arthritis (RA), Abstract FRI0018, European League Against Rheumatism (EULAR) (2002).
Wood, H., Could anti-amyloid-beta immunotherapy do more harm than good? Nature Reviews, Neurology, 1 page (2015).
Wu, Z. et al., Tonic inhibition in dentate gyrus impairs long-term potentiation and memory in an Alzheimer's disease model, Nat. Commun., 5:4159, 25 pages (2014).
Yang, S. et al., Protective Effects of p38 MAPK Inhibitor SB202190 against Hippocampal Apoptosis and Spatial Learning and Memory Deficits in a Rat Model of Vascular Dementia, BioMed Research International, Hindawi Publishing Corporation, vol. 2013, Article ID 215798, 9 pages (2013).
Yasuda, S. et al., p38 MAP kinase inhibitors as potential therapeutic drugs for neural diseases, Cent. Nerv. Syst. Agents Med. Chem., 11(1):45-59 (2011).
Zeman et al., Diagnosis of Dementia Using Nuclear Medicine Imagining Modalities, 12 Chapters on Nuclear Medicine, pp. 199-230 (2011).
Zhu et al., CD45 Deficiency Drives Amyloid-$\beta$ Peptide Oligomers and Neuronal Loss in Alzheimer's Disease Mice, The Journal of Neuroscience, 31(4):1355-1365 (2011).
Zhu et al., CD45RB Is a Novel Molecular Therapeutic Target to Inhibit A$\beta$ Peptide-Induced Microglial MAPK Activation, PLoS One, 3(5):1-12 (2008).

* cited by examiner

CHANGE IN LATENCY FROM FIRST TO LAST TEST DAY IN MORRIS WATER MAZE

P=0.007 for VX-745 1.5 mg/kg aged rats compared to vehicle-treated aged rats

CHANGE IN DISTANCE FROM FIRST TO LAST TEST DAY IN MORRIS WATER MAZE

P=0.012 for VX-745 1.5 mg/kg aged rats compared to vehicle-treated aged rats

FUNCTIONAL RECOVERY AFTER ISCHEMIC STROKE:

Limb Placing and 7- and 20-point Neuroscore Results

FUNCTIONAL RECOVERY AFTER ISCHEMIC STROKE:

Cylinder Change Results

METHODS FOR TREATING NEUROLOGIC DISORDERS

BACKGROUND OF THE INVENTION

The intracellular enzyme p38 MAPKα has been best characterized as a regulator of pro-inflammatory cytokines (IL-1β and TNFα) production from macrophages and microglia, and is considered a therapeutic target in Alzheimer's disease (Munoz, 2010); the primary rationale being the reduction of inflammatory mediators from microglia and their impact downstream of Aβ: excitotoxity, synaptic dysfunction, and tau phosphorylation. IL-1β-p38 MAPKα may also directly modulate memory formation and cognitive function through effects on long-term potentiation/depression (MacAfoose, 2009; Barrientos, 2012). However, no p38 MAPKα anatagonists have been developed for AD due to previous unavailability of blood-brain-barrier (BBB) penetrant compounds. Given their known action on pro-inflammatory cytokine production, P38 MAPK inhibitors otherwise have been evaluated in a wide range of non-CNS diseases (rheumatoid arthritis, inflammatory bowel disease, COPD) as anti-inflammatory agents. Thus, there remains an important unmet need to develop p38 MAPKα anatgonists that penetrate the BBB as treatments of AD and other neurological conditions.

DETAILED DESCRIPTION OF CERTAIN EMBODIMENTS OF THE INVENTION

Definitions

Figure 1:
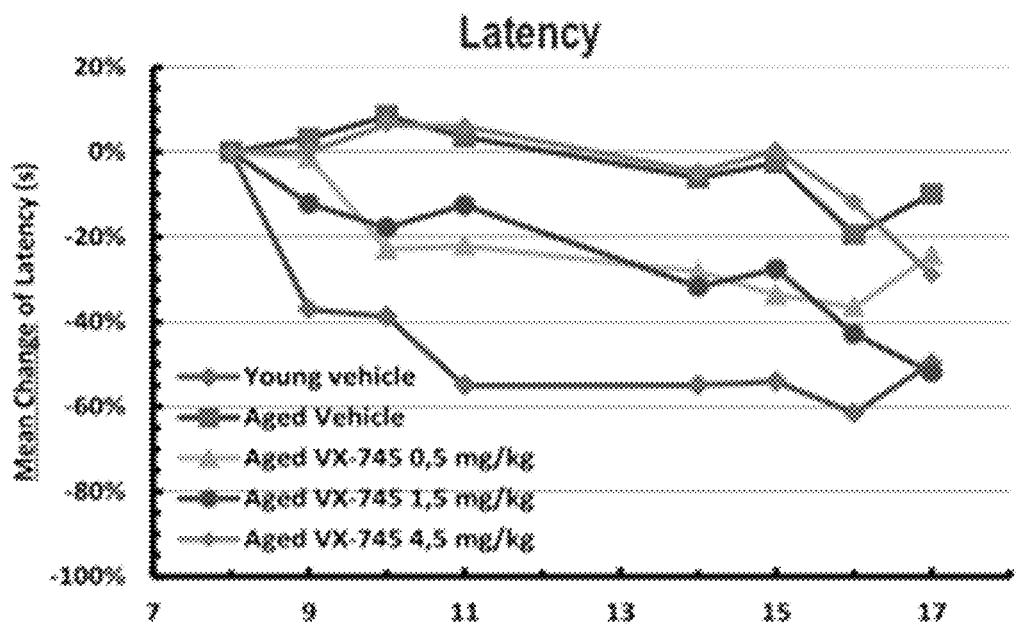
FIG. 1 depicts the change in latency results of the Morris Water Maze test comparing 0.5 mg/kg, 1.5 mg/kg, and 4.5 mg/kg doses of VX-745 in aged rats.

Carrier: The term "carrier" refers to any chemical entity that can be incorporated into a composition containing an active agent (e.g., a p38 inhibitor) without significantly interfering with the stability and/or activity of the agent (e.g., with a biological activity of the agent). In certain embodiments, the term "carrier" refers to a pharmaceutically acceptable carrier. An exemplary carrier herein is water.

Combination. As used herein, the term "combination," "combined," and related terms refers to a subject's simultaneous exposure to two or more therapeutic agents in accordance with this invention. For example, an agent of the present invention (e.g., a p38 inhibitor) may be administered with another therapeutic agent simultaneously or sequentially in separate unit dosage forms or together in a single unit dosage form. Accordingly, the present invention provides, among other things, dosing regimens that involve administering at least an agent of the present invention (e.g., a p38 inhibitor), an additional therapeutic agent, and a pharmaceutically acceptable carrier, adjuvant, or vehicle (the pharmaceutically acceptable carrier, adjuvant, or vehicle typically being in association with one or both of the p38 inhibitor and the additional therapeutic agent).

Formulation. The term "formulation" refers to a composition that includes at least one active agent (e.g., VX-745) together with one or more carriers, excipients or other pharmaceutical additives for administration to a patient. In general, particular carriers, excipients and/or other pharmaceutical additives are selected in accordance with knowledge in the art to achieve a desired stability, release, distribution and/or activity of active agent(s) and which are appropriate for the particular route of administration.

Mid-dose. The term "mid-dose" as used herein refers to a dose of VX-745 that delivers to the blood stream sufficient to inhibit p38 MAPK mediated intracellular signaling events after cytokine and other receptor activation, but below the therapeutically effective amount of VX-745 to produce inhibition an anti-inflammatory effect via reduction of cytokine production. In some embodiments, the term "mid dose" refers to a dose that achieves blood concentrations one-half, one-third, one-fourth, one-fifth, one-sixth, one-seventh, one-eighth the blood concentration required to reduce inflammation and treat a disorder other than a neurological disorder in accordance with the present invention. For example, the mean blood concentration of VX-745 in the treatment of rheumatoid arthritis is approximately 75 ng/mL, consistent with whole blood IC50 for VX-745 inhibition of cytokine production (anti-inflammatory activity) of 65-80 ng/mL. In some embodiments a "mid-dose" of VX-745 provides a blood concentration of between about 15 and 45 ng/mL, or between 20 and about 40 ng/mL, or between about 25 and about 35 ng/mL, or between about 30 and about 40 ng/mL, wherein said blood concentration achieves inhibition of cytokine signaling but not inhibition of cytokine production Parenteral. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Patient. The term "patient", as used herein, means a mammal to which a formulation or composition comprising a formulation is administered, and in some embodiments includes humans.

Pharmaceutically acceptable carrier, adjuvant, or vehicle. The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Therapeutic agent. As used herein, the phrase "therapeutic agent" refers to any agent that elicits a desired biological or pharmacological effect when administered to an organism.

Therapeutically effective amount and effective amount. As used herein, and unless otherwise specified, the terms "therapeutically effective amount" and "effective amount" of an agent refer to an amount sufficient to provide a therapeutic benefit in the treatment, prevention and/or management of a disease, disorder, or condition, e.g., to delay onset of or minimize (e.g., reduce the incidence and/or magnitude of) one or more symptoms associated with the disease, disorder or condition to be treated. In some embodiments, a composition may be said to contain a "therapeutically effective amount" of an agent if it contains an amount that is effective when administered as a single dose within the context of a therapeutic regimen. In some embodiments, a therapeutically effective amount is an amount that, when administered as part of a dosing regimen, is statistically likely to delay onset of or minimize (reduce the incidence and/or magnitude of) one or more symptoms or side effects of a disease, disorder or condition.

Treat or Treating. The terms "treat" or "treating," as used herein, refer to partially or completely alleviating, inhibiting, delaying onset of, reducing the incidence of, yielding prophylaxis of, ameliorating and/or relieving a disorder, disease, or condition, or one or more symptoms or manifestations of the disorder, disease or condition.

Unit Dose. The expression "unit dose" as used herein refers to a physically discrete unit of a formulation appropriate for a subject to be treated (e.g., for a single dose); each unit containing a predetermined quantity of an active agent selected to produce a desired therapeutic effect when administered according to a therapeutic regimen (it being understood that multiple doses may be required to achieve a desired or optimum effect), optionally together with a pharmaceutically acceptable carrier, which may be provided in a predetermined amount. The unit dose may be, for example, a volume of liquid (e.g., an acceptable carrier) containing a predetermined quantity of one or more therapeutic agents, a predetermined amount of one or more therapeutic agents in solid form (e.g., a tablet or capsule), a sustained release formulation or drug delivery device containing a predetermined amount of one or more therapeutic agents, etc. It will be appreciated that a unit dose may contain a variety of components in addition to the therapeutic agent(s). For example, acceptable carriers (e.g., pharmaceutically acceptable carriers), diluents, stabilizers, buffers, preservatives, etc., may be included as described infra. It will be understood, however, that the total daily usage of a formulation of the present invention will be decided by the attending physician within the scope of sound medical judgment. The specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts. In some embodiments, a unit dose of VX-745 is about 1 mg, 3 mg, 5 mg, 10 mg, 15 mg, 20 mg, 25 mg, 30 mg, 35 mg, 40 mg, 45 mg or 50 mg.

VX-745—a p38 MAPK Inhibitor

Many extracellular stimuli, including pro-inflammatory cytokines and other inflammatory mediators, elicit specific cellular responses through the activation of mitogen-activated protein kinase (MAPK) signaling pathways. MAPKs are proline-targeted serine-threonine kinases that transduce environmental stimuli to the nucleus. Once activated, MAPKs activate other kinases or nuclear proteins through phosphorylation, including potential transcription factors and substrates. The novel mammalian reactivating protein kinase (p38/RK) MAPKs are stress-activated protein kinases that mediate responses to cellular stresses and inflammatory signals.

Recent human genetic data indicate major drivers of Alzheimer's are dysregulated microglia and neuroinflammation. As in vitro data indicate IL-1$\beta$-p38 MAPK system is a key regulator of microglia/inflammation, p38 MAPK is recognized as a significant therapeutic target (Munoz, 2010). P38 MAPK is also produced within neurons and appears to have a direct role in modulating intra-neuronal signaling events related to the neurologic function (McAfoose, 2009; Correa, 2012). However, the effects of inhibiting p38 MAPK in a chronic model of Alzheimer's are unknown due to previous unavailability of blood-brain-barrier (BBB)-penetrant p38 MAPK antagonists (Munoz, 2010). As a result, also previously unknown is the relative importance and effects of inhibiting inflammation versus other effects of p38 MAPK inhibition such as intra-neuronal signaling of IL-1$\beta$ or TNF$\alpha$.

The role of p38 MAPK in the various stages of inflammation has prompted the discovery of several compounds capable of inhibiting p38 (SB203580, RWJ 67657, L-167307, VX-745, RPR200765A and others). See, e.g., Kumar et al., "p38 MAP Kinases: Key Signaling Molecules as Therapeutic Targets for Inflammatory Diseases," *Nature Reviews*, 2:717-726 (2003); Brown et al., "p38 MAP kinase inhibitors as potential therapeutics for the treatment of joint degeneration and pain associated with osteoarthritis," *J. Inflammation* 5:22 (2008), the entirety of each of which is incorporated herein by reference. These pharmacological inhibitors are cytokine-suppressive anti-inflammatory drugs responsible for in vitro and in vivo inhibition of lipopolysaccharide-induced tumor necrosis factor-$\alpha$ (TNF-$\alpha$) production, and have been developed in accordance with the primary pharmacologic action presumed to being reduction of inflammation; for example, in clinical studies doses were administered to achieve blood concentrations that met or exceeded the whole blood IC50 (inhibitory concentration for 50% maximal effect) for inhibition of cytokine (IL-1$\beta$ or TNF$\alpha$).

VX-745 is a selective small-molecule inhibitor of p38 MAPK previously developed by Vertex Pharmaceuticals for the treatment of rheumatoid arthritis (RA).

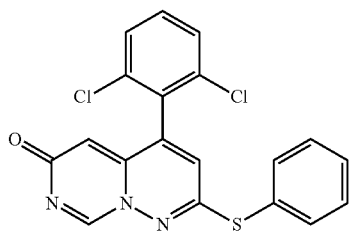
VX-745

The inhibition of MAPK by VX-745 blocks the downstream synthesis of inflammatory cytokines TNF-α and IL-1β. The whole blood IC50 for VX-745 is 150 to 180 nM, or between 65 and 80 ng/mL (Duffy, 2011). Because VX-745 exhibited significant anti-inflammatory activity in rodent arthritis models, Vertex initiated clinical studies in human rheumatoid arthritis (RA). In a phase 2 clinical treated with 250 mg VX-745 b.i.d, which achieved mean plasma drug concentrations of approximately 75 ng/m, significant reduction in inflammatory markers and clinical improvement was demonstrated. However, patients experienced adverse events, including gastrointestinal effects such as diarrhea and abdominal pain, and elevations in liver transaminases. Moreover, VX-745 is known to penetrate the blood brain barrier (BBB) in animals. Indeed, VX-745 achieves brain concentrations 1.7 times that in plasma. Animals subjected to very high doses of VX-745 experienced adverse neurological effects, although these adverse events were not observed in humans. Despite validating the proof-of-concept for the inhibition of p38 MAPK as a treatment for RA, VX-745 was discontinued in favor of a non-blood-brain-barrier-penetrant compound, VX-702, which would allow for greater inhibition of p38 MAPK mediated cytokine production outside the brain for diseases such as rheumatoid arthritis without incurring risk of neurologic side effects.

Another study utilizing VX-745 as a reference compound in an arthritis model demonstrated that 10 mg/kg dose of VX-745 was not as effective at inhibiting paw swelling as other compounds assayed. See Chopra et al., "Pharmacological profile of AW-814141, a novel, potent, selective and orally active inhibitor of p38 MAP kinase," *International Immunopharmacology*, 10: 467-473 (2010), the entirety of which is incorporated herein by reference.

In an osteoarthritis model, VX-745 showed statistically significant inhibition of knee degeneration compared to control animals when administered to rats at 50 mg/kg. VX-745 was also assayed in a hyperalgesia model and showed significant inhibition of hyperalgesic response when administered to rats at doses of 30 mg/kg, 10 mg/kg and 3 mg/kg. The researchers discovered that the mice exhibited hyperalgesia at the 3 mg/kg, 10 mg/kg and 30 mg/kg doses. However, the researchers observed minimal effect at the 3 mg/kg dose. See Brown et al., "p38 MAP kinase inhibitors as potential therapeutics for the treatment of joint degeneration and pain associated with osteoarthritis," *J. Inflamm.*, 5:22 (2008), the entirety of which is incorporated herein by reference.

Without wishing to be bound by theory, it is believed that the clinical failures of p38 inhibitors to treat chronic inflammatory conditions such as rheumatoid arthritis are due to redundancy of the inflammatory (cytokine production) pathways. Such redundancy results in the upregulation of feedback loops when p38 MAPK-mediated cytokine production is chronically inhibited, leading to an overall lack of efficacy.

Methods of the Invention

In a 2-week pilot study in aged, 26 month old Tg2576 mice, VX-745 treated mice had lower amyloid plaque load than control animals, but otherwise drug effect could not be assessed as little inflammation was evident. This information, combined with reports that transgenic Aβ mice demonstrate a compensatory phaygocytic (antiinflammatory) microglial phenotype, the decision was made not to conduct further work in the mouse. Instead, for a thorough dose-response study to predict human doses, the aged rat model was chosen; in which increased pro-inflammatory cytokine expression is well established, and as such reflects better the inflammatory milieu in human aging and AD (Barrientos, 2012). An additional advantage of the rat model is that with VX-745 very good pharmacokinetics-pharmacodynamic correlation between rat and human had previously been established (between studies in rat adjuvant arthritis model and human clinical trials in RA). A second dose-response study in rats was conducted in a model of functional recovery after ischemic stroke.

Surprisingly, in both studies, the best effects on neurologic function were at a mid-dose level that achieved blood concentrations that were below those required to inhibit cytokine production and therefore unable to produce an anti-inflammatory effect, but sufficient to inhibit p38 MAP mediated intracellular signaling events. More surprisingly, it was found that the effects on neurologic function at a higher dose that did produce a demonstrable anti-inflammatory effect in the brain had less of an effect neurologic function than the mid-dose level. Thus, in some embodiments, the present invention encompasses the appreciation that the potency of VX-745 for inhibition of intracellular signaling after cytokine receptor activation is approximately twice that for inhibition of cytokine production; providing a means to administer VX-745 to achieve inhibition of cytokine signaling, and with it improvement in neurologic function, without inhibiting cytokine production resulting in a general anti-inflammatory state.

As described above, in some embodiments, the present invention provides a method of treating a neurologic disorder in a patient in need thereof comprising administering to the patient an amount of VX-745 sufficient to inhibit cytokine signaling while not substantially affecting cytokine production. In some embodiments, the present invention provides a method of treating a neurologic disorder by administering an amount of VX-745 sufficient to inhibit IL-1beta signaling while not substantially affecting IL-1beta production.

As used herein, the term "neurologic disorder" refers to any one or more of Alzheimer's Disease, Mild Cognitive Impairment, Vascular Dementia, Lewy Body Dementia, and Dementias; Parkinson's Disease; Functional recovery after Stroke; Fronto-Temporal dementia (FTD) and Parosysmal Spastic Paraplegia (PSP) and other Tauopathies; Cognitive Frailty; Chronic Tinnitus; and Huntington's Disease. In certain embodiments, a neurological disorder treated by a provided method is selected from Alzheimer's Disease, Mild Cognitive Impairment, Vascular Dementia, Lewy Body Dementia, and Dementias; Parkinson's Disease; Functional recovery after Stroke; Fronto-Temporal dementia (FTD) and Parosysmal Spastic Paraplegia (PSP) and other Tauopathies; Cognitive Frailty; Chronic Tinnitus; and Huntington's Disease.

As used herein, the phrase "amount sufficient to inhibit cytokine (i.e., IL-1beta) signaling while not substantially affecting cytokine (i.e., IL-1beta) production" refers to a dose of VX-745 that results in patient blood concentrations at less than half of that required to inhibit cytokine production. In some embodiments, the "amount sufficient to inhibit cytokine (i.e., IL-1beta) signaling not substantially affecting cytokine (i.e., IL-1beta) production" is a dose of VX-745 that results in patient blood concentration that is 50% lower than, 60% lower than, 70% lower than, 80% lower than, or 90% lower than blood concentration required to inhibit cytokine (i.e., IL-1beta) production.

As used herein, the phrase "while not substantially affecting cytokine (i.e., IL-1beta) production" means that a provided method results in a blood concentration of VX-745 that does not measurably inhibit cytokine production.

Without wishing to be bound by any particular theory, one aspect of the present invention is the appreciation that VX-745 achieves inhibition of cytokine signaling at a much lower blood concentration than that required for inhibition of cytokine inhibition. A further aspect of the present invention is the appreciation that VX-745 achieves a positive neurologic affect at the lower concentration where cytokine signaling is inhibited but cytokine production is not affected.

In some embodiments, the present invention provides a method of improving cognition comprising administering an amount of VX-745 sufficient to inhibit cytokine signaling while not substantially affecting cytokine production. In some embodiments, the present invention provides a method of improving cognition by administering an amount of VX-745 sufficient to inhibit IL-1beta signaling while not substantially affecting IL-1beta production.

As used herein, the term "improving cognition" refers to any measurable improvement in cognitive decline or other cognitive symptoms of any neurologic disorder, such as Alzheimer's Disease, Mild Cognitive Impairment, Vascular Dementia, Lewy Body Dementia, and Dementias; Parkinson's Disease; Functional recovery after Stroke; Fronto-Temporal dementia (FTD) and Parosysmal Spastic Paraplegia (PSP) and other Tauopathies; Cognitive Frailty; Chronic Tinnitus; and Huntington's Disease.

In some embodiments, the present invention provides a method of improving neurologic function by administering an amount of VX-745 sufficient to inhibit cytokine signaling while not substantially affecting cytokine production. In some embodiments, the present invention provides a method of improving neurologic function by administering an amount of VX-745 sufficient to inhibit IL-1beta signaling while not substantially affecting IL-1beta production.

In some embodiments, a provided method comprises administering to a patient in need thereof VX-745 at a dose sufficient to achieve blood concentrations that result in inhibition of cytokine signaling but wherein said blood concentration is not sufficient to result in inhibition of cytokine production. In certain embodiments, a provided method comprises administering to a patient in need thereof VX-745 at a dose sufficient to achieve blood concentrations that result in inhibition of IL-1beta signaling but wherein said blood concentration is not sufficient to result in inhibition of IL-1beta production.

In certain embodiments, a provided method comprises administering to a patient in need thereof VX-745, or a pharmaceutically acceptable composition thereof, at a dose providing a blood concentration of between about 15 and about 45 ng/mL. In some embodiments, a provided method comprises administering to a patient in need thereof a dose of VX-745, or a pharmaceutically acceptable composition thereof, providing a blood concentration of between about 20 and about 40 ng/mL, or between about 25 and about 35 ng/mL, or between about 30 and about 40 ng/mL.

In certain embodiments, the present invention provides a method of treating a neurologic condition comprising administering to a patient in need thereof a dose of VX-745, or a pharmaceutically acceptable composition thereof, providing a blood concentration of between about 15 and 45 ng/mL, or between about 20 and about 40 ng/mL, or between about 25 and about 35 ng/mL, or between about 30 and about 40 ng/mL.

In some embodiments, the present invention provides a method of treating a neurologic condition comprising administering to a patient in need thereof a dose of VX-745, or a pharmaceutically acceptable composition thereof, providing a blood concentration of between about 15 and 45 ng/mL, or between about 20 and about 40 ng/mL, or between about 25 and about 35 ng/mL, or between about 30 and about 35 ng/mL, wherein said blood concentration achieves inhibition of cytokine signaling but not inhibition of cytokine production.

Combination Therapies

In certain embodiments, the present invention provides a method of treating a neurological disorder comprising administering to a subject a low dose of VX-745 together with one or more additional therapeutic agents. In some embodiments, the present invention provides a method of treating a neurologic disorder comprising administering to a subject a therapeutically effective amount of VX-745 sufficient to inhibit cytokine signaling while not substantially affecting cytokine production in combination with one or more additional therapeutic agents selected from cholinesterase inhibitors, N-methyl-D-aspartate antagonists, vitamin E, antidepressants, anxiolytics, antipsychotics, mood stabilizers and sleep aids.

Representative cholinesterase inhibitors include, without limitation, donepezil (Aricept®), rivastigmine (Exelon®), galantamine (Razadyne®) and tacrine (Cognex®).

Representative antidepressants include, without limitation, bupropion (Wellbutrin®), citalopram (Celexa®), fluoxetine (Prozac®), mirtazapine (Remeron®), paroxetine (Paxil®), sertraline (Zoloft®), trazodone (Desyrel®), venlafaxine (Effexor®), nortriptyline (Pamelor®) and desipramine (Norpramine®).

Representative anxiolytics include, without limitation, lorazepam (Ativan®) and oxazepam (Serax®).

Representative antipsychotics include, without limitation, aripiprazole (Abilify®), clozapine (Clozaril®), haloperidol (Haldol®), olanzapine (Zyprexa®), quetiapine (Seroquel®), risperidone (Risperdal®) and ziprasidone (Geodon®).

Representative mood stabilizers include, without limitation, carbamazepine (Tegretol®) and divalproex (Depakota®).

Representative sleep aids include, without limitation, zolpidem, zaleplon and chloral hydrate.

Representative N-methyl-D-aspartate antagonists include, without limitation, memantine (Namenda®).

In some embodiments, the present invention provides a method of treating a neurologic disorder comprising administering to a subject a therapeutically effective amount of VX-745 sufficient to inhibit cytokine signaling while not substantially affecting cytokine production in combination with one or more additional therapeutic agents selected from the group consisting of exenatide (Byetta®), varenicline, PF-04360365, rivastigmine, LY450139, ST101, bryostatin, EVP-6124, atomoxetine, HF0220, resveratrol, galantamine, PF-01913539, semagacestat, 3APS, immunoglobulin, dimebon, alpha-tocopherol, BAY85-8101, estrogen, progesterone, ACC-001, ginko biloba, nicergoline, piracetam, NIC5-15, xaliproden (SR57746A), indomethacin, DMXB-A, LY2062430, 11-C PIB, bapineuzumab, etanercept, ramipril, interferon beta-1a, simvastatin, lipoic acid, fish oil, curcumin, PF-04447943, folate, vitamin B6, vitamin B12, leuprolide, INM-176, AH110690, tryptophan, SK-PC-B70M, BMS-708163, escitalopram, TRx0014, BAY94-9172, cerebrolysin, epigallocatechin-galate, SB-742457, lithium, rosiglitazone, divalproex, SAR110894D, PRX-03140, CX516 (Ampalex), nicotinamide, rasagiline, AC-1202 (Ketasyn®), enduramide, neramexane, razadyne, NS 2330 (Tesofensine®), tamibarotene, acitretin, methylphenidate, mifepristone, ZT-1, AFFITOPE AD01, AFFITOPE AD02, GSK239512, GSK933776, SR57667B, PPI-1019, MPC-7869, AZD3480, PAZ-417, solanezumab, masitinib (AB1010), BAY1006578, docosahexaenoic acid, QS-21, MNI-558, reminyl retard, flutemetamol, estradiol, medroxyprogesterone, valproate, T-817MA, AZD1446, AAB-003 (PF-05236812), modafinil, raloxifene, atorvastatin, doxycycline, trazadone, sodium oxybate, huperzine A, lutein, zeaxanthin, AC-3933, dextroamphetamine, EPAX 1050TG, SRA-333, MNI-168, CAD106, SGS742, NP031112, SSR180711C, GSI-953, prazosin, MEM 1003, AndroGel, AVE1625, cyclophosphamate, TC-5619-238, MK0249, lecozotan, circadin, MEM 3454, PPI-1019, UB 311, PF-04494700, ABT-089, LY451395, E2020, Rofecoxib, PF-03654746, EHT 0202 etazolate, DCB-AD1, ONO-2506P0, EGb761®, gantenerumab, florbetapir, ELND005, prednisone, novasoy, ginseng, pioglitazone, caprylidene, ABT-288, ABT-384, nefiracetam, AQW051, Pitavastatin, naproxen sodium (Aleve®), lornoxicam, AN-1792, SR57667B, melatonin, SAM-531, MK0952, MK0677, IFN-alpha2A, BAY 94-9172, PYM50028, lecozotan SR, thalidomide, tramiprosate, FK962, IVIG, R05313534, bifeprunox, LNK-754, ELND005, NSA-789, ramelteon, Florbetaben, SRA-444, VP4896, celecoxib, hydrocodone, GSI-136, Zolpidem, MK3328, metformin, CTS21166, elontril, ibuprofen, posiphen tartrate, JNJ-39393406, testosterone, BRL-049653, BMS-708163, SAM-315, ketoconazole, fluconazole, warfarin, E2609, AZD0328, LY2886721, CHF 5074, E2212, acetaminophen, LY2811376, ABT-126, melatonin, GSK1034702, armodafinil, depakote, gemfibrozil, AL-108, levetiracetam, and quinacrine.

Pharmaceutical Compositions

In some embodiments, a provided method comprises administering to a patient a pharmaceutical composition comprising VX-745 together with one or more therapeutic agents and a pharmaceutically acceptable carrier, adjuvant, or vehicle. In some embodiments, the present invention provides a pharmaceutical composition comprising a dose of VX-745 together with one or more therapeutic agents and a pharmaceutically acceptable carrier, adjuvant, or vehicle, wherein the dose of VX-745 results in a blood concentration of between about 5 and 45 ng/mL, between about 10 and 45 ng/mL, between about 15 and 45 ng/mL, or between about 20 and about 40 ng/mL, or between about 25 and about 35 ng/mL, or between about 30 and about 40 ng/mL. In some embodiments, the dose of VX-745 results in a blood concentration of between about 5 and 35 ng/mL, between about 10 and 30 ng/mL, between about 10 and 25 ng/mL, between about 5 and 20 ng/mL, or between about 10 and 20 ng/mL.

In certain embodiments, pharmaceutically acceptable compositions of this invention are formulated for oral administration. Pharmaceutically acceptable compositions of this invention may be orally administered in any orally acceptable dosage form including, but not limited to, capsules, caplets, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

The quantities of the compounds of the present invention that are combined with the carrier materials to produce a composition in a single dosage form will vary depending upon the patient and the particular mode of administration. Preferably, provided compositions should be formulated so that a dosage of between 1-50 mg/day of VX-745 can be administered to a patient receiving these compositions. Examples of compositions include compositions formulated to administer dosages of between 1-10 mg, 10-25 mg or 25-50 mg per day of VX-745 to the patient receiving these compositions. In other embodiments of the invention, compositions include compositions formulated to administer dosages of between 3-5 mg, 5-10 mg, 10-20 mg, 20-30 mg, 30-40 mg or 40-50 mg, per day of the inhibitor to the patient receiving these compositions. In some embodiments, the composition is formulated into doses containing 1 mg, 3 mg, 5 mg, 10 mg, 20 mg, 25 mg, 30 mg or 50 mg of the active composition. Dosing regimens for these formulations may include but are not limited to single administration dosing, once, twice, or three times daily dosing, weekly dosing, and monthly dosing. In some embodiments, a provided composition is formulated to provide 40 mg/day of VX-745.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

EXEMPLIFICATION

Example 1

Morris Water Maze

Background

Recent human genetic data indicate major drivers of Alzheimer's are dysregulated microglia and neuroinflammation. In addition, in vitro data indicate IL-1β-p38 MAPK system may impact memory through effects on Long-Term Potentiation (LTP) and Long-Term Depression (LTD) in neurons (McAfoose, 2009); and, p38 MAPK has been identified as a mediator of inhibition of LTP by oligomeric AB (Li, 2011). However, the effects of inhibiting p38 MAPK in a chronic model of Alzheimer's are unknown due to previous unavailability of blood-brain-barrier (BBB) penetrant p38 MAPK antagonists (Munoz, 2010). Also, not known is the relative importance of p38 MAPK, and effects on inhibition thereof, of p38 MAPK mediated production of cytokines (IL-1β and TNFα) from microglia versus p38 MAPK mediated cytokine signaling within neurons.

VX745 (BBB penetrant selective p38 MAPKalpha antagonist) inhibits both IL-1beta production and signaling, with potency for signaling two-fold higher. To re-position for Alzheimer's after previous non-CNS clinical experience, VX-745 was tested in aged rat model; and in a second supportive study in a rat model of functional recovery after ischemic stroke.

Purpose

The primary objective of this study was to investigate whether pre-treatment with compound VX-745 alleviates cognitive defects in aged rats. Plasma concentration of VX-745 was determined with LC-MS/MS at the end of the study from samples collected 1 hour post dosing. In addition, protein levels of PSD95 in ventral cortex and hippocampus, and levels of IL-1β in the hippocampus were analyzed by specific ELISA assays to evaluate the potential anti-inflammatory effects of VX-745 in the brain Methods Altogether 60 female aged (20-24 months) and 15 young adult female Fischer Rats (2-3 months) were used for the experiment. Rats were treated with oral gavage twice-a-day until the sampling (23 days) with vehicle or VX-745 0.5, 1.5 or 4.5 mg/kg. Learning and memory deficits were analyzed with Morris water maze (MWM) one week after starting the treatment.

Test Animals

All animal experiments were carried out according to the National Institute of Health (NIH) guidelines for the care and use of laboratory animals, and approved by the National Animal Experiment Board, Finland. Altogether 60 female aged (20-24 months) and 15 young (2-3 months) adult female Fischer rats (Charles River, France) were used for the experiment. Animals were housed at a standard temperature (22±1° C.) and in a light-controlled environment (lights on from 7 am to 8 pm) with ad libitum access to food and water. Animals were grouped as follows:

Group 1: 15 Aged Rats treated with Vehicle p.o. BID
Group 2: 15 Aged Rats treated with VX-745 (0.5 mg/kg) p.o. BID
Group 3: 15 Aged Rats treated with VX-745 (1.5 mg/kg) p.o. BID
Group 4: 15 Aged Rats treated with VX-745 (4.5 mg/kg) p.o. BID
Group 5: 15 Young adult control rats treated with Vehicle p.o. BID Drug Delivery and Rat Identification The rats were assigned to the treatment groups equally based on their body weight and visible platform pre-training performance to ensure that both good and poor learners were equally present in all treatment groups. The treatment was given by oral gavage twice-a-day until the sampling. Vehicle was 1% Pluronic F108 and dosing volume was 5 ml/kg. Administration of vehicles and test compounds was done at 7-9 am and 3-5 pm on the pre-testing phase. On the days of behavioral testing, the treatment was given minimum 1 hour prior to first test trial. Test compounds were formulated and stored according to the instructions provided by the sponsor. The rats were marked accordingly with permanent marker to the tail. Records were kept about treatment groups and daily treatment times.

Morris Water Maze

Water maze task was originally designed by Morris et al. (J Neurosci Methods. 1984; 11: 194 47-60). Testing was performed in a large dark-colored tank (200 cm in diameter) filled with clear water at a temperature of 25.0±1.0° C. A submerged platform (square platform: 10×10 cm; 1.5 cm below water surface) was placed in the middle of the of the NW quadrant. The starting locations, which were labeled N, NE, E, SE, S, SW, W, NW, were located arbitrarily on the pool rim. The rats were lowered into the pool with their nose pointing toward the wall at one of the starting points. The release point adjacent to platform location (NW) was not used.

Before the compound treatment was started, the visible platform pre-training was performed to determine whether any non-cognitive performance impairments (e.g. visual impairments and/or swimming difficulties) were present, which might affect performance on the place or probe trials. After the visible platform pre-training was completed, the data was analyzed and the rats were assigned to the different treatment groups based on their pre-training performance. This procedure was performed to ensure that each treatment group consisted equally both good and poor performers in the cued version of the water maze task.

Acquisition training—weeks 1 (days 8-11) & 2 (days 15-18): After completion of cued trials, acquisition (place) trials were executed to determine the rat's ability to learn the spatial relationship between distant cues and the submerged escape platform which remained in the same location for all place trials. The starting points were randomized (NW is not used). The rats received four trials (15 min apart, 60 s maximum for each trial) each day for 4 days/week. Latency and path length (distance) were evaluated.

Probe trial (day 19): A single probe trial was conducted 24 hours after the last place trial to evaluate memory retention. The platform was removed from the pool and the rat was placed into the pool in the quadrant opposite to one the platform was placed before. The rats were allowed to swim for 60 s without the platform. During the probe trial, the time spent in target quadrant and target platform annulus (36-cm-diameter circular area surrounding platform), and crosses over the target platform position were measured. There were no positive or negative effects of VX-745 treatment in any of the probe parameters, and so otherwise are not discussed in this application.

Endpoint, Blood Samples and Tissue Processing for PK 257

One hour after the last vehicle or VX-745 morning dosing, the animals (10 per dosing group) were deeply anesthetized with pentobarbital and blood samples were collected by cardiac puncture. 500 µl of blood was collected into EDTA microtubes, centrifuged, and plasma collected. The brains were perfused with heparinized saline, and the brains were collected. Right hemisphere was post-fixed by immersion in 4% PFA in 0.1 M PB for 24 h. After a brief wash with phosphate buffer, the hemisphere was cryoprotected in 30% sucrose in PB for 2-3 days, after which it was frozen on liquid nitrogen and stored at −80° C. for optional future immunohistochemical analysis. Left hemisphere was dissected to ventral and dorsal cortex, hippocampus and remaining brain fraction and fresh frozen on dry ice.

Cortex and hippocampal soluble extracts were analyzed for PSD95 content using an ELISA kit (Cusabio Biotech Ltd., #CSB-EL006938RA, Lot 031154387), while the levels of Il-1β were analyzed only from hippocampus (R&D Systems, #RLB00, Lot 308544).

Figure 2:
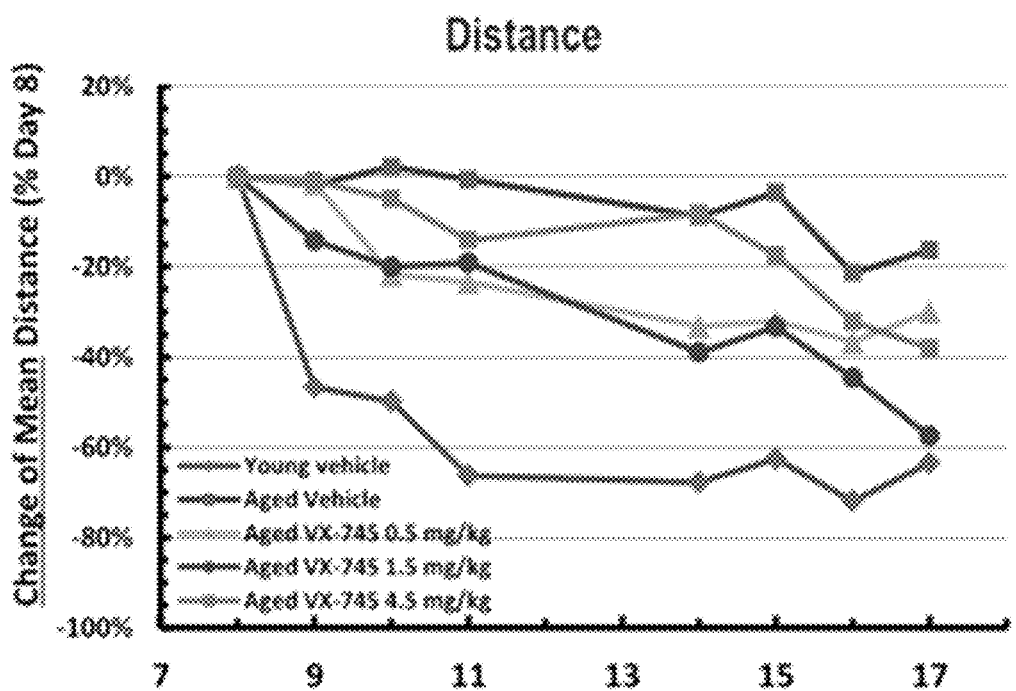
FIG. 2 depicts the change in distance results of the Morris Water Maze test comparing 0.5 mg/kg, 1.5 mg/kg, and 4.5 mg/kg doses of VX-745 in aged rats.

Plasma samples were processed using acetonitrile precipitation and then analyzed for VX745 drug concentration by LC-MS/MS Results Vehicle-treated young rats demonstrated effective learning with rapid reduction in MWM latency/distance with sequential testing. Aged vehicle-treated rats appeared cognitively impaired, exhibiting longer times and distances than young rats, and little improvement during the study. VX-745-treated aged rats exhibited greater progressive shortening of swim time and distance, evidence of improved cognitive performance. For both latency and distance the 1.5 mg/kg dose of VX-745 had the greatest effect, with performance in this group of rats being approximately equal to that of young vehicle-treated rats on last test Day 17. In comparison to vehicle-treated aged rats, the 1.5 mg/kg dose group demonstrated statistically significant better performance at day 17 for both latency and distance (p=0.013 and 0.0.019, respectively. See FIG. 1. Moreover, as for distance there was significant worse performance at the first test day (p=0.018), the data also were also analyzed after normalization by comparing change in latency and distance from first test day to last test day; by this analysis as well, the 1.5 mg/kg treated aged rats performed significantly better than vehicle-treated aged rats with a p=0.007 for change in latency and p=0.012 for change in distance. See FIG. 2.

PSD95 is a protein present in post-synaptic structures thought to contribute to clustering of receptors and ion channels that assure post-synaptic response. PSD95 levels have been shown to be reduced in Alzheimer's disease and to be increased in animal models when treated with anti-inflammatory agents (Frautchy, 2001) The analysis of the PSD95 protein in the showed a statistical trend towards higher levels of PSD95 in the VX-745 high-dose (4.5 mg/kg) group compared to the aged vehicle-treated group (p=0.063 by Mann-Whitney rank sum test).

The analysis of IL-1β levels in the hippocampus indicated that there was a trend to higher levels in aged rats. In the VX-745 high-dose (4.5 mg/kg) group, IL-1 β levels were similar to those of young rats and were lower relative to the aged vehicle-treated group (p=0.038 by Mann-Whitney rank sum test).

Figure 3:
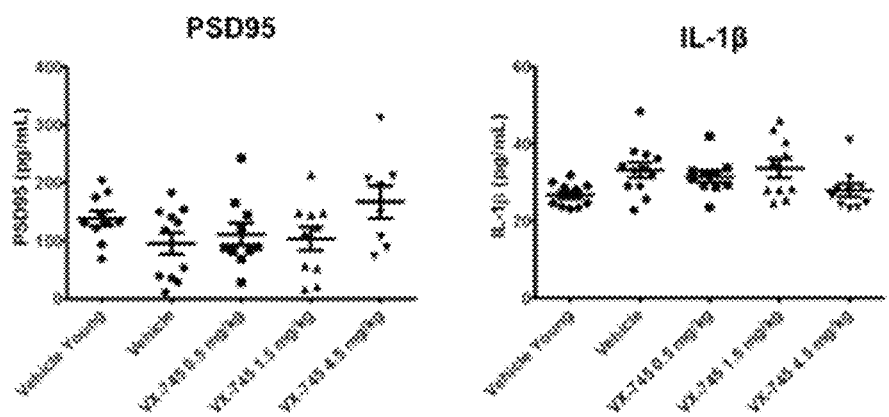
FIG. 3 depicts protein levels of VX-745.

There were no evident effects of the 1.5 mg/kg dose level, which otherwise demonstrated significant improvement of performance in the Morris-Water-Maze test, on either PSD95 or IL-1β; indicating the effects in the Morris Water Maze test level at this dose level were not mediated by inhibition of cytokine production (i.e. via an anti-inflammatory effect). See FIG. 3.

Figure 4:
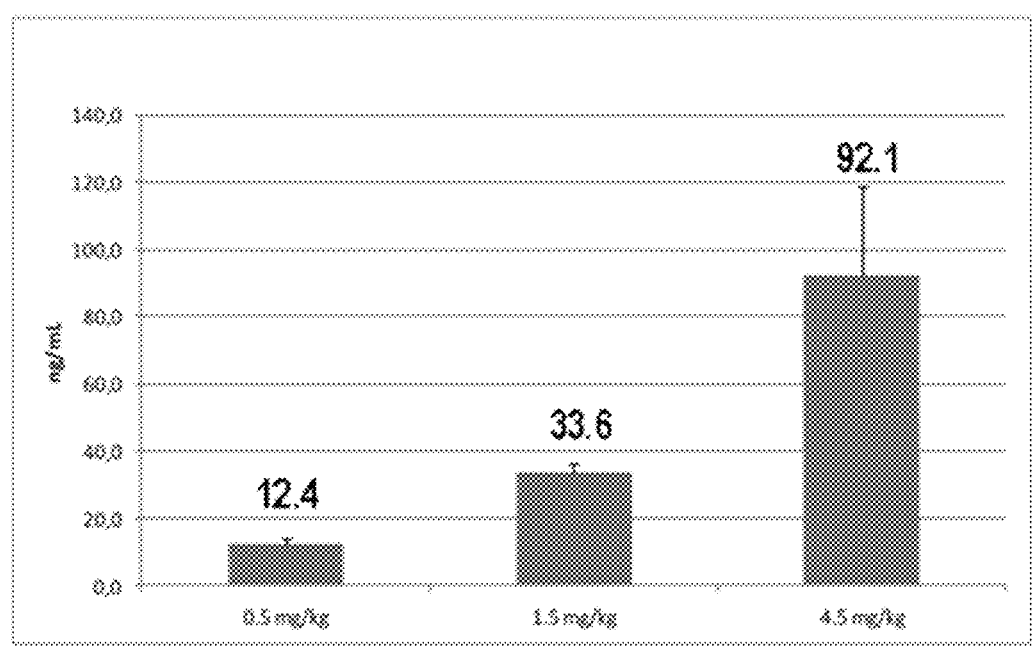
FIG. 4 depicts the median plasma concentration of VX-745 at 0.5 mg/kg, 1.5 mg/kg, and 4.5 mg/kg doses of VX-745.

VX-745 plasma drug levels one hour after last dose increased in a dose proportional manner. See FIG. 4. Based on the known plasma drug profile in rats from previous pre-clinical studies, the one-hour post dose level at steady-state should approximate the steady-state Caverage ($C_{AVG}$). As prior, previously undisclosed studies indicates that the VX-745 IC50 in human systems for inhibition of IL-1β production is approximately half that for inhibition of IL-1β signaling, the 1.5 mg/kg reached drug concentrations required for blocking IL-1β signaling; only 4.5 mg/kg reached concentrations exceeding whole blood IC50 for IL-1β production.

Conclusions

The present invention is directed, in part, to the discovery of a positive cognition effect of p38 MAPK inhibition in a chronic Alzheimer's animal model at a dose level that was insufficient to produce an anti-inflammatory effect. Consistent with that finding PK/PD correlations indicate that the effect is mediated by inhibition of IL-1beta signaling, rather than by suppression of IL-1beta production.

Example 2

Transient MCAO in Rats—Functional Recovery

The objective of this study was to investigate whether chronic twice-a-day treatment with VX-745 started at 48 hours post-occlusion provides sensory-motor recovery and neuroprotection in rats subjected to 120 min middle cerebral artery occlusion (tMCAO) at day 0. Seven and 20-point Neuroscore tests were performed to study sensory-motor deficits and general condition on days 1, 3, 7, 14, 21, 28, 35 and 42 post-ischemia. Cylinder test was performed on days 7, 14, 21 and 35 post-ischemia and limb-placing tests on days 1, 3, 7, 14, 21, 28, 35 and 42.

Infarct volume was evaluated by T2-MRI at 24 h post-ischemia and rats were allocated to treatment groups based on the lesion data on day 2 and treatment was started after MRI on day 2.

Methods—Male Sprague-Dawley rats were subjected to twice-a-day chronic treatment with VX-745 starting at 48 h after 120 min tMCAO. Lesion size was measured at 24 h with MRI and rats were allocated to dosing groups on day 2 (tMCAO performed on day 0) based on lesion size and limb placing results. Rats were treated with 2 different doses and underwent sensorimotor behavioral test throughout the experiment. Seven and 20-point Neuroscore and limb placing tests were performed to study sensory-motor deficits and general condition before occlusion and on days 1, 3, 7, 14, 21, 28, 35 and 42 post-ischemia. Cylinder test was performed before occlusion and on days 7, 14, 21 and 35 post-ischemia.

Animals. Altogether 45 adult male Sprague Dawley rats, purchased from Charles River Laboratories (Sulzfeld, Germany), and weighing 250-300 g were used for the experiment. Animals were housed at a standard temperature (22±1° C.) and in a light-controlled environment (lights on from 7 am to 8 pm) with ad libitum access to food and water. Animals were grouped as follows:

Group A: 15 tMCAO animals treated twice-a-day with vehicle from day 2 to 42 (5 ml/kg, p.o)

Group B: 15 tMCAO animals treated twice-a-day with VX-745 from day 2 to 42 (1.5 mg/kg, p.o.).

Group C: 15 tMCAO animals treated twice-a-day with VX-745 from day 2 to 42 (4.5 mg/kg, p.o.).

Transient MCAO

Transient focal cerebral ischemia was produced by MCA occlusion at Day 0 in male Sprague-Dawley rats according to Koizumi with modifications (Koizumi et al. Jpn. J. Stroke 8:1-8, 1986). The rats were anesthetized with 5% isoflurane (in 70% $N_2O$ and 30% $O_2$; flow 300 ml/min). During the operation the concentration of anesthetic was reduced to 1.0-2.0%. The rectal temperature was maintained at 37.0±1.0° C. with a homeothermic blanket system. After midline skin incision, the right common carotid artery (CCA) was exposed, and the external carotid artery (ECA) was ligated distal from the carotid bifurcation. A 0.22-mm diameter monofilament nylon thread, with blunted tip, was inserted 22-23 mm into the internal carotid artery (ICA) up to the origin of MCA. After the monofilament insertion, CCA was occluded for 2 hours with a suture. After 120 min of ischemia, the MCA blood flow was restored by removal of the filament and the suture. The wound was closed, disinfected, and the animals were allowed to recover from anesthesia. The rats were carefully monitored for possible post-surgical complications after the tMCAO. The rats were fed with standard laboratory diet suspended in tap water after the tMCAO. To prevent dehydration all rats were given an i.p. injection of saline (4 mL per rat) once or twice-a-day as needed.

Drug Delivery. VX-745 or vehicle was administered p.o. (5 ml/kg) starting after MRI at 48 h post-ischemia (i.e. Day 2) and continued twice-a day (morning and afternoon) until endpoint day 42.

General Health Status and Humane End-Points. Animals were monitored twice a day by laboratory personnel. In the case that the general health status of an animal was significantly worsened, the rat was terminated by an overdose of $CO_2$, and decapitated. Definitions of acceptable endpoints include: no spontaneous movements and inability to drink or eat in 24-h observation period, massive bleeding, spontaneous inflammation, missing anatomy, swelling or tumors larger than 20 mm, and inability to right itself in 30 sec period.

Treatment Allocation

MRI acquisitions in vivo for all rats were performed at 24 h after tMCAO (i.e. Day 1) Lesion size, tissue viability (T2 in milliseconds) and brain edema was determined using absolute T2-MRI. Rats were allocated to treatment groups on day 2 based on the lesion data and treatment was started on day 2.

Twenty-Point Neuroscore

A 20-point Neuroscore test was used to assess post-ischemic motor and behavioral deficits. The neurological test was conducted by a blinded investigator at pre-stroke (baseline) and on days 1, 3, 7, 14, 21, 28, 35 and 42 post-ischemia.

The following parameters were analyzed:
Paw placement (max. score 4)
Righting reflex (max. score 1) visual forepaw reaching (max. score 2)
Circling (max. score 4)
Contralateral (max. score 1)
Grip strength (max. score 2)
Motility (max. score 3)
General condition (max. score 3)
The maximum score for a normal rat was 20 points.

Seven-Point Neuroscore

Concurrently a seven-point Neuroscore test was used to assess post-ischemic motor and behavioral deficits (modified from Zausinger et al., 2000). The neurological test was conducted by blinded investigator at: pre-stroke (baseline) and on days 1, 3, 7, 14, 21, 28, 35 and 42 post-ischemia.

Grade 6: Normal extension of both forelimbs towards the floor when lifted gently by the tail.
Grade 5: Consistent flexion of the forelimb contralateral to the injured hemisphere, varying from mild wrist flexion and shoulder adduction to severe posturing with full flexion of wrist, elbow, and adduction with internal rotation of the shoulder.
Grade 4: Dysfunctional rats with a consistently reduced resistance to lateral push towards the paretic side.
Grade 3: Rats circling towards the paretic side if pulled and lifted by the tail.
Grade 2: Rats circling towards the paretic side if pulled by the tail.
Grade 1: Rats circling spontaneously towards the paretic side.
Grade 0: Rats with no spontaneous motion.

Limb Placing Test

The Limb Placing test was used to assess the sensory-motor integration of fore- and hind-limbs responses to tactile and proprioceptive stimulation (de Ryck et al., 1989; Jolkkonen et al., 2000). Limb Placing Test was conducted by blinded investigator before tMCAo (baseline) and at days 1, 5, 7, 14, 21, 28 and 35 post-ischemia.

The test had seven limb placing tasks, which were scored:
2 points, the rat performs normally;
1 point, the rat performs with a delay (>2 sec) and/or incompletely
0 point, the rat does not perform normally
The both sides of the body were tested.

In the first task, the rat was suspended 10 cm above the table surface. Non-lesioned rats stretch both forelimbs towards the table. On the second task the rat was held facing towards the table, resting its forelimbs on the table edge. The forelimb was gently pulled down, off of the table, and subsequent retrieval and limb placement was checked. Non-lesioned rats replace both limbs on the table. The third task was the same as the second, except that the rat was not able to see the table or make vibrissal contact, since the head is held upward at a 45° angle. The rats were next placed along the table edge to check the lateral placing of the fore- (the fourth task) and hindlimbs (the fifth task). The limbs were pulled down as described in task 2, and limb retrieval was scored accordingly. In the sixth task the rats were placed with their rear end at the edge of the table, with the hindlimbs resting on the table edge. The hindlimbs, 1 at a time, were gently pulled down and off of the table. If necessary, retrieval of the limb to the original resting place on the table edge could be stimulated by pushing the animal towards the table edge. In the seventh task the rat was placed at the table edge, facing away from the table surface. The forelimbs of the rat placed on the edge of the table, and the rat was gently pushed from behind toward the edge. Injured rats could not keep their grip and the injured limb slipped off the edge. The maximum points for a normal rat was 14 points.

Cylinder Test.

The cylinder test (modified from Schallert and Tillerson in Innovative models of CNS disease: from molecule to therapy. Clifton, N.J., Humana, 1999) is used to quantify the forelimb use asymmetry, while the animal is rearing against the wall of the home cage. The test was performed before tMCAO and on days 7, 14 and 21 after tMCAO. The rats were monitored as they move freely in their home cage. Contacts made by each forepaw with the cage wall while rearing are scored by a blinded observer. A total of 15-20 contacts are recorded for each animal, and the number of impaired (left) and non-impaired forelimb contacts as percentage of total contacts is calculated.

Results

Figure 5:
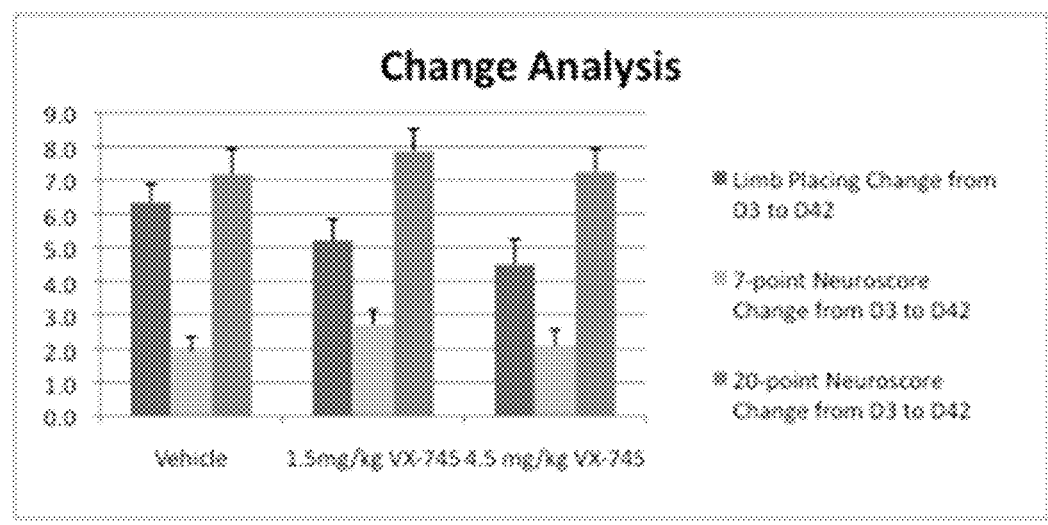
FIG. 5 depicts the functional recovery results for limb placing and 7- and 20-point neuroscoring after ischemic stroke comparing 0.5 mg/kg, 1.5 mg/kg, and 4.5 mg/kg doses of VX-745 in aged rats.
Figure 6:
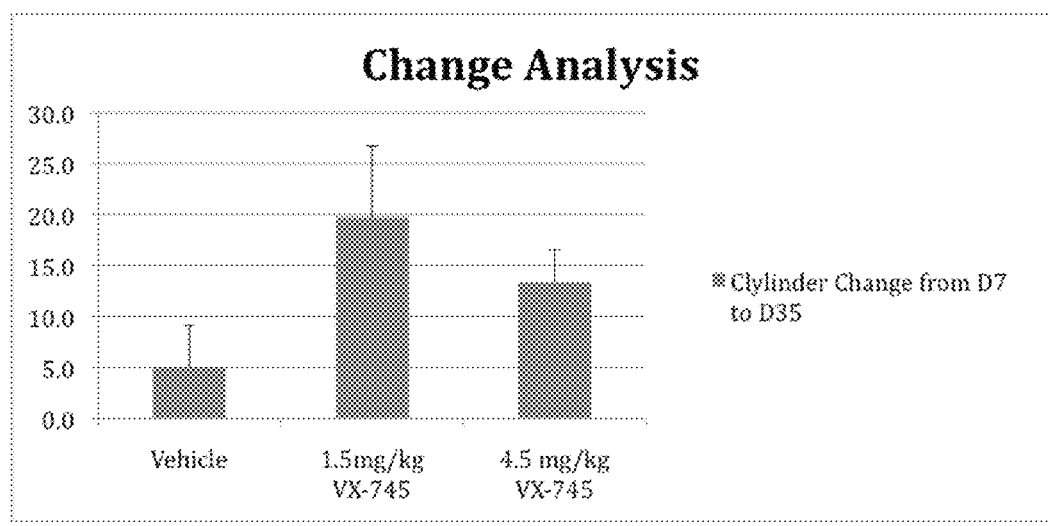
FIG. 6 depicts the functional recovery results for the cylinder test after ischemic stroke comparing 0.5 mg/kg, 1.5 mg/kg, and 4.5 mg/kg doses of VX-745 in aged rats.

Functional recovery was analyzed change from baseline (day 3) to end point (day 42) was analyzed for limb placing and 7- and 20-point. See FIG. 5. In cylinder test the change from day 7 to day 35 was analyzed. The 1.5 mg/kg VX-745 dose group seems to do consistently better than the 4.5 mg/kg VX-745 group. In addition, the 1.5 mg/kg VX-745 dose group demonstrated a trend (p=0.088, two-sided t-test) towards increased improvement in change in cylinder test performance from day 7 to day 35 relative to vehicle-treated animals; an trend that was not evident in the 4.5 mg/kg dose group. See FIG. 6.

Conclusions

Results on functional recovery measured with limb placing, 7- or 20-point neuroscore in this study demonstrated substantial functional improvement after tMCAO in the vehicle treated animals and administration of 1.5 mg/kg VX-745 or 4.5 mg/kg not further improve functional recovery by these measures. Minimal functional recovery was evident with vehicle treatment in the cylinder test, and a trend (p=0.088) towards improvement compared to vehicle treatment was evident with 1.5 mg/kg VX-745 in change in performance on the cylinder test from Day 7 to day 35. For all the measures, in the change analysis, the 1.5 mg/kg VX-745 dose group seemed to do consistently better than the 4.5 mg/kg VX-745 group further supporting the concept that any positive effects of VX-745 on neurologic function occur at dose level that does not have a measurable anti-inflammatory effect, consistent it with that dose level not achieving blood concentrations that impact cytokine production; while a dose level that achieves blood concentrations that inhibit cytokine production and as a result has an anti-inflammatory has lesser effects on neurologic function.

I claim:

1. A method of improving cognition in a patient in need thereof comprising administering to the patient a pharmaceutically acceptable composition comprising an effective amount of VX-745 that is sufficient to inhibit cytokine signaling without substantially inhibiting IL-1beta production.

2. The method according to claim 1, wherein the improvement in cognition results in a measurable decrease in the rate of cognitive decline.

3. A method of improving cognition in a patient in need thereof comprising administering to the patient a pharmaceutically acceptable composition comprising an effective amount of VX-745 that is sufficient to provide a blood concentration from about 15 to about 45 ng/mL, or from about 20 to about 40 ng/mL, or from about 25 to about 35 ng/mL, or from about 30 to about 40 ng/mL.

4. The method according to claim 1, further comprising administering an additional therapeutic agent.

5. The method of claim 4, wherein the additional therapeutic agent is selected from the group consisting of cholinesterase inhibitors, N-methyl-D-aspartate antagonists, vitamin E, antidepressants, anxiolytics, antipsychotics, mood stabilizers and sleep aids.

6. The method of claim 1 wherein the pharmaceutically composition comprising VX-745 is formulated for oral administration.

7. The method of claim 3, wherein the pharmaceutically composition comprising VX-745 is formulated for oral administration.

* * * * *

UNITED STATES PATENT AND TRADEMARK OFFICE
CERTIFICATE OF CORRECTION

PATENT NO. : 9,579,322 B2
APPLICATION NO. : 14/794469
DATED : February 28, 2017
INVENTOR(S) : John Jahangir Alam Page 1 of 1

It is certified that error appears in the above-identified patent and that said Letters Patent is hereby corrected as shown below:

In the Specification

At Column 5, Lines 1-12, please delete:

" 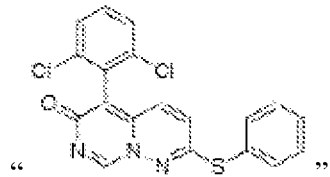 "

And insert:

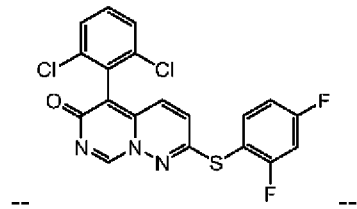

-- --

Signed and Sealed this
Twenty-fourth Day of October, 2017

Joseph Matal
*Performing the Functions and Duties of the
Under Secretary of Commerce for Intellectual Property and
Director of the United States Patent and Trademark Office*